United States Patent [19]
Yoshioka et al.

[11] Patent Number: 5,929,068
[45] Date of Patent: Jul. 27, 1999

[54] OPTICALLY ACTIVE BENZOTHIAZEPINE COMPOUNDS AND PROCESS FOR PREPARING THE SAME

[75] Inventors: Ryuzo Yoshioka, Mishima-gun; Shin-ichi Yamada, Takarazuka; Takeji Shibatani, Kobe, all of Japan

[73] Assignee: Tanabe Seiyaku Co., Ltd., Osaka, Japan

[21] Appl. No.: 08/758,577

[22] Filed: Dec. 3, 1996

[30] Foreign Application Priority Data

Dec. 5, 1995 [JP] Japan .................... 7-316154

[51] Int. Cl.[6] ............... A01N 43/46; C07D 267/02
[52] U.S. Cl. ........................... 514/215; 540/552
[58] Field of Search ................. 514/215; 540/552

[56] References Cited

U.S. PATENT DOCUMENTS

| | | | |
|---|---|---|---|
| 3,562,257 | 2/1971 | Kugita et al. | 260/239.3 |
| 4,567,175 | 1/1986 | Takeda et al. | 514/211 |
| 4,931,587 | 6/1990 | Piselli | 562/401 |
| 5,013,834 | 5/1991 | Piselli | 540/491 |
| 5,128,469 | 7/1992 | Nishimoto et al. | 540/491 |
| 5,134,139 | 7/1992 | Kawai et al. | 514/211 |
| 5,183,922 | 2/1993 | Rizzi et al. | 560/7 |

FOREIGN PATENT DOCUMENTS

| | | |
|---|---|---|
| 0392543 | 10/1990 | European Pat. Off. |
| 0488210 | 6/1992 | European Pat. Off. |
| 46-43785 | 12/1971 | Japan . |
| 53-18038 | 6/1978 | Japan . |
| 63-13994 | 3/1988 | Japan . |
| 3-157378 | 7/1991 | Japan . |

OTHER PUBLICATIONS

H. Inoue, et al., "Synthesis of 1,5–Benzothiazepine Derivatives. IV. Resolution of dl–cis–3–Acetoxy–5–[2–(dimethylamino)ethyl]–2,3–dihydro–2–(p–methoxyphenyl)–1, 5–benzothiazepin–4(5H)–one Hydrochloride," *UDC*, vol. 93, No. 6 (1973), pp. 729–732.

J. Jacques et al., *Enantiomers, Racemates and Resolutions*, John Wiley & Sons (New York), 1981, pp. 223–250.

H. Kugita et al., "Synthesis of 1,5–Benzothiazepine Derivatives. III," *Chemical and Pharmaceutical Bulletin*, vol. 19, No. 3 (1971), pp. 595–602.

Schwartz et. al., "Enantioselective Synthesis . . . Diltiazem Group", *J. Org. Chem.*, vol. 57 (Jan. 31, 1992), No. 3, pp. 851–856.

Kojie–Prodie et. al., "Absolute Conformation and Configuration of . . . ", *Helv. Chim. Acta*, vol. 67 (1984), Fasc. 3, pp. 916–926.

*Primary Examiner*—Richard L. Raymond
*Assistant Examiner*—Tamthom T. Ngo
*Attorney, Agent, or Firm*—Finnegan, Henderson, Farabow, Garrett & Dunner, L.L.P.

[57] ABSTRACT

An optically active salt of 1,5-benzothiazepine compound of the formula (I) or (II):

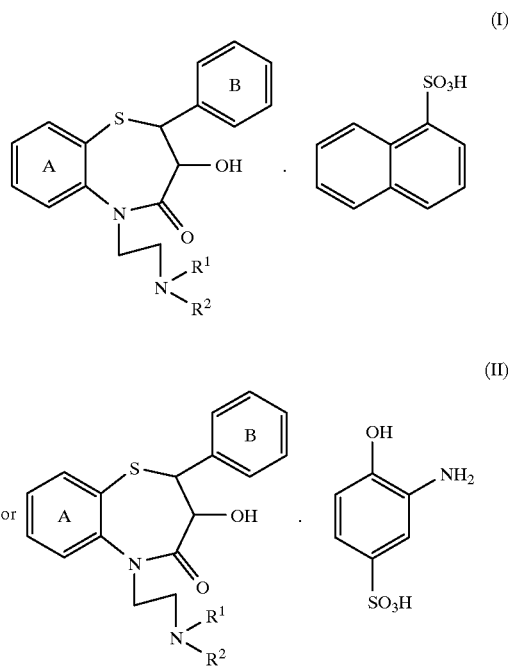

wherein each of Ring A and Ring B is a substituted or unsubstituted benzene ring, and $R^1$ and $R^2$ are the same or different and each is a lower alkyl group, can be prepared by resolving a racemic salt of 1,5-benzothiazepine compound of the formula (I) or (II) by means of preferential crystallization.

18 Claims, No Drawings

OPTICALLY ACTIVE BENZOTHIAZEPINE COMPOUNDS AND PROCESS FOR PREPARING THE SAME

The present invention relates to optically active 1,5-benzothiazepine compounds and a process for preparing the same. The optically active 1,5-benzothiazepine compounds obtained by the present invention are important as intermediates for preparing diltiazem hydrochloride [(2S,3S)-cis-3-acetoxy-5-[2-(dimethylamino) ethyl]-2,3-dihydro-2-(4-methoxyphenyl)-1,5-benzothiazepin-4(5H)-one hydrochloride] etc., which are useful as a coronary vasodilator.

PRIOR ART

Hitherto, there have been known some processes for preparing the optically active 1,5-benzothiazepine compounds.

Examples of these processes include, for instance (i) a process which comprises treating racemic 3-(2-aminophenylthio)-2-hydroxy-3-(4-methoxyphenyl) propionic acid or an ester thereof with an optically active tartaric acid to give two diastereoisomeric salts, collecting the resultant (−)-(2S,3S)-diastereoisomeric salt by utilizing the difference in solubility between the two diastereoisomeric salts, and converting the collected salt into an optically active 1,5-benzothiazepine compound [cf. European Patent First Publication No. 392543/1990], and (ii) a process which comprises treating racemic cis-3-acetoxy-2,3-dihydro-5-[2-(dimethylamino) ethyl]-2-(4-methoxyphenyl)-1,5-benzothiazepin-4(5H)-one with an optically active compound such as D-tartaric acid, quinic acid, dibenzoyl-D-tartaric acid, or d-10-camphor sulfonic acid to give two diastereoisomeric salts, collecting the desired diastereoisomeric salt by utilizing the difference in solubility between the two diastereoisomeric salts, and converting the collected salt into an optically active 1,5-benzothiazepine compound [cf. H. Inoue, S. Takeo, M. JKawazu, H. IKugita YAKJGAKU ZASSHI 93(6) 729–732 (1973)], and the like.

However, with regard to racemic cis-5-[2-(di-lower-alkylamino) ethyl]-2,3-dihydro-3-hydroxy-2-(substituted or unsubstituted phenyl)-1,5-substituted or unsubstituted benzothiazepin-4(5H)-one, processes for optical resolution of the benzothiazepine compound by means of preferential crystallization using an achiral compound as a resolving agent have never been known.

Generally speaking, there has been known the principle of optical resolution of a racemric compound by means of preferential crystallization [J. Jacques, A. Collet and S. H. Wilen/ Enantiomers, Racemates and Resolutions/1981 by John Wiley & Sons, Inc.].

The optical resolution by means of preferential crystallization mentioned above is industrially advantageous, because the resolution method can be carried out without using any particular and expensive resolving agents. But, this method is only applicable to a compound which forms "a racemic mixture" in a solvent. Furthermore, it is unpredictable whether or not a certain compound may form a racemic mixture and whether or not the racemic mixture may be optically resolved by preferential crystallization.

Namely, in order to find a crystalline racemic mixture of benzothiazepine compounds which is applicable to the optical resolution by preferential crystallization, it is essential to prepare various crystals of the benzothiazepine compounds and examine them. Besides, it is well known that most compounds do not form a racemic mixture. Therefore, much effort is needed for finding compounds which satisfy such a requirement.

As a result of intensive studies by the present inventors, it has been found that a certain kind of salt of optically active benzothiazepine compounds can be obtained in high yield by preferential crystallization comprising economical and industrially convenient steps. More concretely, as a result of the studies on various types of salts of (2RS,3RS)-cis-5-[2-(di-lower-alkylamino) ethyl]-2,3-dihydro- 3-hydroxy-2-(substituted or unsubstituted phenyl)-1,5-substituted or unsubstituted benzothiazepin-4(5H)-one and each optical isomer thereof, the present inventors found that 1-naphthalenesulfonic acid addition salt or 2-aminophenol-4-sulfonic acid addition salt of the benzothiazepine compounds are stable, and the acid addition salts form a racemic mixture which can be resolved by preferential crystallization. And hence, the present invention is accomplished based on the above-mentioned findings.

BRIEF DESCRIPTION OF THE INVENTION

An object of the present invention is to provide a novel acid addition salt of an optically active benzothiazepine compound and a process for preparing the same.

DETAILED DESCRIPTION OF THE INVENTION

According to the present invention, an optically active salt of cis-3-hydroxy-1,5-benzothiazepine compound of the formula (I):

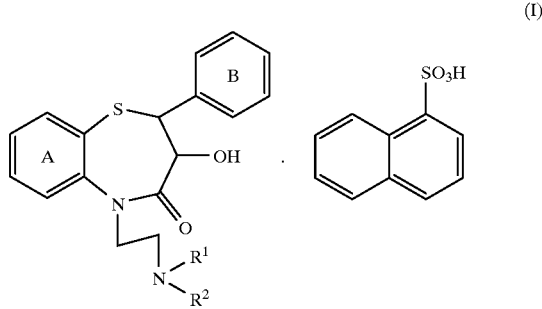

(I)

wherein each Ring A and Ring B is a substituted or unsubstituted benzene ring, and $R^1$ and $R^2$ are the same or different and each is a lower alkyl group, can be prepared by resolving a racemic mixture of the salt of cis-3-hydroxy-1,5-benzothiazepine compound of the formula (I) by means of preferential crystallization.

Moreover, an optically active salt of cis-3-hydroxy-1,5-benzothiazepine compound of the formula (II):

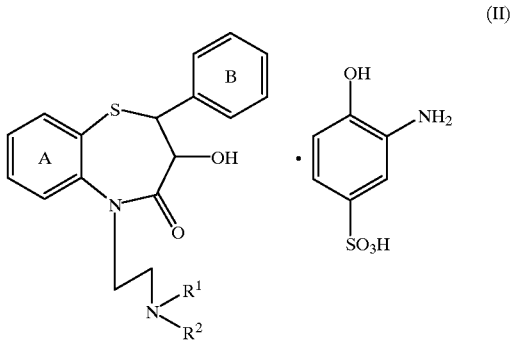

(II)

wherein each Ring A and Ring B is a substituted or unsubstituted benzene ring, and $R^1$ and $R^2$ are the same or different and each is a lower alkyl group, can be prepared by resolving a racemic mixture of the salt of cis-3-hydroxy-1,5-benzothiazepine compound of the formula (II) by means of preferential crystallization.

In the present invention, Ring A and Ring B in the 1,5-benzothiazepine compounds of the formula (I) and (II) may be unsubstituted benzene ring or a benzene ring substituted with a substituent selected from a lower alkyl group, a lower alkoxy group and a halogen atom at any position thereof, and $R^1$ and $R^2$ are the same or different and are a lower alkyl group.

Examples of the lower alkyl group and the lower alkoxy groups mentioned above include straight or branched chain-alkyl group having 1 to 6 carbon atoms (e.g., methyl group, ethyl group, propyl group, isopropyl group, butyl group or isobutyl group) and straight or branched chain-alkoxy group having 1 to 6 carbon atoms (e.g., methoxy group, ethoxy group, propoxy group, isopropoxy group or butoxy groups). Examples of the halogen atom include chlorine atom, bromine atom, fluorine atom or iodine atom.

Among them, preferred examples of Ring A include a benzene ring of the formula (V):

(V)

wherein R is a hydrogen atom, a methyl group, a methoxy group or a chlorine atom. Preferred examples of Ring B include a benzene ring substituted with a methoxy group or a methyl group at the 4-position thereof. Preferred examples of $R^1$ and $R^2$ include a methyl group.

Further preferred examples of Ring A include an unsubstituted benzene ring, and further preferred examples of Ring B include a benzene ring substituted with a methoxy group at the 4-position thereof. Further preferred examples of $R^1$ and $R^2$ include a methyl group.

In the process of the present invention, the optical resolution of a racemic mixture of the salt of 1,5-benzothiazepine compound (I) or (II) by preferential crystallization can be carried out by preparing a supersaturated solution of the racemic salt (I) or (II) and inoculating seed crystals of the desired optically active salt of the corresponding (2S,3S)- or (2R,3R)-isomer into the solution to precipitate preferentially the same crystals as the inoculated salt.

The supersaturated solution of the racemic salt of 1,5-benzothiazepine compound (I) or (II) can be prepared by a conventional manner, for example, by the steps of (1) dissolving the racemic salt of 1,5-benzothiazepine compound (I) or (II) in a solvent under heating, and (2) cooling or concentrating the solution, or adding another solvent to the solution (this solvent being able to lower the solubility of the salt (I) or (II) in the solution).

Additionally, a soluble compound (e.g., hydrochloric acid, ammonium chloride and methylamine hydrochloride) may be added to the supersaturated solution in order to increase the degree of supersaturation or the stability of a supersaturated solution.

Examples of the solvent to be used for the preparation of the supersaturated solution include, for example, water; an alcohol such as methanol, ethanol or isopropanol; a ketone such as acetone or methylethylketone; an ether such as dioxane or tetrahydrofuran; an amide such as acetamide or dimethylformamide; and a mixture thereof.

In the present invention, it is necessary for the resolution of racemic salt (I) or (II) to inoculate seed crystals into the supersaturated solution. On the other hand, when the solute in the supersaturated solution is a salt of (2S,3R)-rich or (2R,3S)-rich isomer, it is not always necessary to inoculate seed crystals because the excess isomer spontaneously crystallizes out and the resultant crystals work as seed crystals.

Although the amount of seed crystals to be used is not particularly limited, the more seed crystals that are used, the more the resolution can be easily carried out and promoted. However, it is preferred to use the seed crystals in an amount of less than about 10 w/w % of salt of the 1,5-benzothiazepine compound in the solution. Meanwhile, in view of the purpose of use thereof, it is preferable that the seed crystals to be used have a high optical purity.

The optical resolution by preferential crystallization can be carried out repeatedly by adding the same racemic mixture as used in the previous preferential crystallization to a mother liquor obtained after the isolation of crystals, preparing a supersaturated solution of the salt in accordance with the manner described above, and inoculating thereto seed crystals of the enantiomer of the salt which was used previously.

Additionally, the racemic salt mentioned above may be added either in the form of a solid or a solution. Both optically active isomers (i.e.,(2S,3S)-isomer and (2R,3R)-isomer thereof) of the salt (I) or (II) can be obtained as crystals by repeating the above-mentioned steps of addition of the racemic salt and preferential crystallization.

When carrying out the present invention in an industrial scale, the optically active benzothiazepine compound can be obtained by batchwise resolution as described above. Both optically active isomers thereof can be simultaneously obtained by using an apparatus which comprises two columns arranged in parallel or series, or a tank having two compartments and inoculating seed crystals of the two different isomer salts into the columns or the compartments, respectively.

The obtained optically active salt of cis-3-hydroxy-1,5-benzothiazepine compound (I) or (I) may be converted into the corresponding free base, i.e., an optically active cis-3-hydroxy-1,5-benzothiazepine compound of the formula (III):

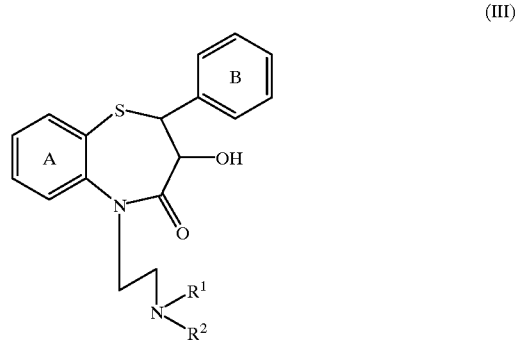

(III)

wherein the symbols are the same as defined above.

The conversion of the optically active salt (I) or (II) into the free base (III) can be easily carried out in accordance with a conventional manner, for example, by dissolving the salt (I) or (II) in a solvent, adding a base to the solution, and collecting the resultant crystals. The conversion also can be carried out by extracting the solution obtained after addition of the base with another solvent and removing the solvent by evaporation.

The solvent used in the conversion step is not particularly limited and any solvent which dissolves the optically active salt of cis-3-hydroxy-1,5-benzothiazepine compound (I) or (II) can be used. Examples of the solvent include water; an alcohol such as methanol, ethanol or isopropanol; a ketone such as acetone or methylethylketone; an ether such as dioxane or tetrahydrofuran; an amide such as acetamide or dimethylformamide, and a mixture thereof.

Examples of the base include an inorganic base such as sodium hydroxide, potassium hydroxide, lithium hydroxide, calcium hydroxide, magnesium hydroxide, potassium carbonate, sodium carbonate, sodium hydrogen carbonate or ammonium hydroxide and an organic base such as methylamine, dimethylamine, trimethyl amine, ethylamine, diethyl amine, triethylamine, isopropylamine, diisopropylamine, pyrrolidine, piperidine or piperadine.

The base mentioned above can be used in an amount of 1–1.5 moles, preferably 1.0 mole, to 1 mole of the optically active salt of 1,5-benzothiazepine compound (I) or (II).

As the solvent used for extraction of the optically active 1,5-benzothiazepine compound (III), a solvent in which the compound (III) is soluble and a resultant sulfonate of the used base is insoluble, may be used preferably. Examples of the extraction solvent include methyl acetate, ethyl acetate, dichloromethane, chloroform, benzene and toluene.

The obtained optically active cis-3-hydroxy-1,5-benzothiazepine compound (III) may be converted into an optically active 1,5-benzothiazepine compound of the formula (IV):

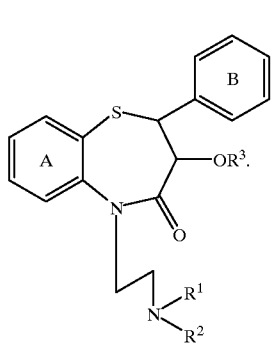

(IV)

wherein $R^3$ is a lower alkanoyl group, and the other symbols are the same as defined above, or a pharmaceutically acceptable salt thereof.

That is, the optically active 3-hydroxy-1,5-benzothiazepine compound (III) can be converted into the corresponding optically active 1,5-benzothiazepine compound (IV) or a pharmaceutically acceptable salt thereof by a conventional method disclosed in U.S. Pat. No. 3,562,257, Japanese Patent Second Publication (Kokoku) No.43785/1971, Japanese Patent Second Publication (Kokoku) No.18038/1978, Japanese Patent Second Publication (Kokoku) No.13994/1988 or Japanese Patent First Publication (Kokai) No.157378/1991.

For example, the compound (IV) can be prepared by condensing the compounds (III) with a compound of the formula (VI):

$R^3$OH  (VI)

wherein $R^3$ is a lower alkanoyl group, or a reactive derivative thereof.

The lower alkanoyl group($R^3$) means a straight or branched chain-alkanoyl group having 2 to 6 carbon atoms such as acetyl group, propionyl group, isopropionyl group, butanoyl group, pentanoyl group or hexanoyl group.

A racemic salt of 1,5-benzothiazepine compound (I) or (II) to be used as the starting material of the present invention is a novel compound. The starting material (I) or (II) can be prepared by treating the 1,5-benzothiazepine compound (III) with 1-naphthalenesulfonic acid or a salt thereof, or 2-aminophenol-4-sulfonic acid or a salt thereof in an appropriate solvent. For example, the starting material can be prepared by dissolving the 1-5-benzothiazepine compound (III) and 1-naphthalenesulfonic acid or 2-aminophenol-4-sulfonic acid in an appropriate solvent under heating, cooling the solution, and collecting the precipitated crystals by filtration.

Preferred examples of the solvent used in the preparation of the starting material (I) or (II) include water and an alcohol such as methanol, ethanol or propanol. The solvent may be used alone or as a mixture of two or more solvents mentioned above. Among them, a mixture of water and an alcohol is preferable.

Meanwhile, the 1,5-benzothiazepine compound (III) is disclosed in Chemical Pharmaceutical Bulletin, 19, p.595 (1971), etc.

The optical purity of compound (I), (II) or (III) obtained by the present invention was determined by high performance liquid chromatography (HPLC) using a chiral column under the following analytical conditions.

Conditions for HPLC analysis:

Column: CHIRALCEL OD (manufactured by Daicel Chemical Industries, LTD.)

4.6×250 mm

Mobile phase: n-Hexane: Ethanol: Diethylamine= 85:15:0.1

Flow Rate:0.5 ml/min

Detection: UV-254 nm

Temperature: 35° C.

The present invention is illustrated in more detail by the following Reference Examples and Examples, but should not be construed to be limited thereto.

REFERENCE EXAMPLE 1

Preparation of (±)-(2RS, 3RS)-cis-5-[2-(dimethylamino) ethyl]-2,3-dihydro-3-hydroxy-2-(4-methoxyphenyl)-1,5-benzothiazepin-4(5H)-one. 1-naphthalenesulfonate.

Sodium 1-Naphthalenesulfonate (6.91 g;30 mmol) is dissolved in water (35 ml) under heating, and thereto is added 1N hydrochloric acid (30 ml) and a solution of (±)-(2RS, 3RS)-cis-5-[2-(dimethylamino) ethyl]-2,3-dihydro-3-hydroxy-2-(4-methoxyphenyl)-1,5-benzothiazepin-4(5H)-one (9.31 g;25 mmol) in hot methanol(47 ml). The mixture is allowed to stand under ice-cooling for 20 hours, and the precipitated crystals are collected by filtration. The collected crystals are dried at 50° C. to give the above-captioned (±)-(2RS, 3RS)-racemic salt (13.50 g; yield:93.0%).

M.p. 136–138° C.; IR (KBr) cm$^{-1}$:3425, 3045, 1660, 1500, 1465, 1295, 1175, 1105, 1040, 770, 680, 610. NMR (200 MHz, CDCl$_3$) δ :2.88 (s, 3H), 2.95 (s, 3H), 3.04–3.09 (m, 1H), 3.25–3.55 (m, 2H), 3.80 (s, 3H), 4.17–4.35 (m, 2H), 4.43–4.58 (m, 1H), 4.87 (d, 1H) 6.86–8.89 (m, 15H).

REFERENCE EXAMPLE 2

Preparation of (±)-(2RS, 3RS)-cis-5-[2-(dimethylamino) ethyl]-2,3-dihydro-3-hydroxy-2-(4-methoxyphenyl)-1,5-benzothiazepin-4(5H)-one•2-aminophenol-4-sulfonate.

(±)-(2RS, 3RS)-cis-5-[2-(dimethylamino) ethyl]-2,3-dihydro-3-hydroxy-2-(4-methoxyphenyl)-1,5-benzothiazepin-4(5H)-one (7.46 g;20 mmol) and 95%

2-aminophenol-4-sulfonic acid (4.38 g;22 mmol) are dissolved in a mixture of methanol (16 ml) and water (48 ml) under heating. The mixture is allowed to stand under ice-cooling for 20 hours, and the precipitated crystals are collected by filtration. The collected crystals are dried at 50° C. to give the above-captioned (±)-(2RS, 3RS)-racemic salt (10.42 g; yield:92.8%).

M.p. 134–137° C.; IR (KBr) cm$^{-1}$:1660, 1600, 1505, 1465, 1280, 1245, 1170, 1100, 1020, 760, 685, 595. NMR (200 MHz, DMSO-d$_6$) δ :2.81 (s, 6H), 3.05–3.20 (m, 2H), 3.76 (s, 3H), 3.94–4.10 (m, 1H), 4.24 (t, 1H), 4.35–4.55 (m, 1H), 4.83 (d, 1H), 4.92 (d, 1H), 6.52–7.75 (m,11H).

EXAMPLE 1

Optical resolution of (±)-(2RS, 3RS)-cis-5-[2-(dimethylamino) ethyl]-2,3-dihydro-3-hydroxy-2-(4-methoxyphenyl)-1,5-benzothiazepin-4(5H)-one. 1-naphthalenesulfonate by means of preferential crystallization.

(A) (±)-(2RS, 3RS)-cis-5-[2-(Dimethylamino) ethyl]-2,3-dihydro-3-hydroxy-2-(4-methoxyphenyl)-1,5-benzothiazepin-4(5H)-one. 1-naphthalenesulfonate (5.01 g) and the corresponding (+)-(2S,3S)-isomeric salt (0.18 g) are dissolved in an aqueous 50 w/w % dimethylformamide (DMF) solution (20 g) under heating, and the solution is cooled to 25° C. Seed crystals of (+)-(2S,3S)-isomeric salt (20 mg) are inoculated thereto, and the mixture is stirred for 19 hours. The precipitated crystals are collected by filtration, washed with cold 50 w/w % DMF in water and dried at 50° C. to give (+)-(2S,3S)-isomeric salt (0.55 g) mentioned above.

[α]$^{25}_D$:+67.6° (c=1, DMF); Optical purity: 98.4% ee

IR and NMR spectra of the obtained salt are identical with those of the product in Reference Example 1.

(B) To the mother liquor obtained by the above mentioned step (A) is added the above-captioned (±)-(2RS,3RS)-isomeric salt (0.7 g), and the mixture is dissolved under heating. After cooling the solution to 25° C., seed crystals of the corresponding (−)-(2R,3R)-isomeric salt (20 mg) are inoculated to the solution, and the mixture is stirred for 15 hours. The precipitated crystals are collected by filtration, washed with cold 50 w/w % DMF in water and dried at 50° C. to give (−)-(2R,3R)-isomeric salt (0.15 g) mentioned above.

[α]$^{25}_D$: −65.4° (c=1, DMF); Optical purity: 95.2% ee

IR and NMR spectra of the product mentioned above are identical with those of the product in IReference Example 1.

EXAMPLE 2

Optical resolution of (±)-(2RES, 3RS)-cis-5-[2-(dimethylamino) ethyl]-2,3-dihydro-3-hydroxy-2-(4-methoxyphenyl)-1,5-benzothiazepin-4(5H)-one. 1-naphthalenesulfonate by means of preferential crystallization.

(±)-(2RS, 3RS)-cis-5-[2-(Dimethylamino) ethyl]-2,3-dihydro-3-hydroxy-2-(4-methoxyphenyl)-1,5-benzothiazepin-4(5H)-one. 1-naphthalenesulfonate (5.37 g) and the corresponding (−)-(2R,3R)-isomeric salt (0.21 g) are dissolved in an aqueous 50 w/w % DMF solution (20 g) under heating. After cooling the solution to 25° C., seed crystals of (−)-(2R,3R)-isomeric salt (20 mg) mentioned above are inoculated to the solution. The mixture is stirred for 3 hours, and the precipitated crystals are collected by filtration. The collected crystals are washed with cold 50 w/w % DMF in water and dried at 50° C. to give (−)-(2R, 3R)-isomeric salt (0.37 g) mentioned above.

[α]$^{25}_D$:−63.4° (c=1, DMF); Optical purity: 92.3% ee

IR and NMR spectra of the product are identical with those of the product in Reference Example 1.

EXAMPLE 3

Optical resolution of (±)-(2RS, 3RS)-cis-5-[2-(dimethylamino) ethyl]-2,3-dihydro-3-hydroxy-2-(4-methoxyphenyl)-1,5-benzothiazepin-4(5H)-one. 2-aminophenol-4-sulfonate by means of preferential crystallization.

(A) (±)-(2RS, 3RS)-cis-5-[2-(Dimethylamino) ethyl]-2,3-dihydro-3-hydroxy-2-(4-methoxyphenyl)-1,5-benzothiazepin-4(5H)-one. 2-aminophenol-4-sulfonate (5.02 g) and the corresponding (+)-(2S,3S)-isomeric salt (0.25 g) are dissolved in water (160 g) under heating. After cooling the solution to 40° C., seed crystals of the (+)-(2S, 3S)-isomeric salt mentioned above (30 mg) are inoculated to the solution. The mixture is stirred for 7 hours, and the precipitated crystals are collected by filtration. The crystals are washed with cold water and dried at 50° C. to obtain (+)-(2S,3S)-isomer salt (0.49 g) mentioned above.

[α]$^{25}_D$:+86.0° (c=1, MeOH); Optical purity: 97.1% ee

IR and NMR spectra of the product are identical with those of the product in Reference Example 2.

(B) The amount of water in the mother liquor obtained by the above mentioned step (A) is adjusted to 160 g, and the above captioned (±)-(2RS,3RS)-racemic salt (0.42 g) is added thereto. The mixture is heated to make a solution. After cooling the solution to 40° C., seed crystals of the corresponding (−)-(2R,3R)-isomeric salt (30 mg) are inoculated to the solution. The mixture is stirred for 5 hours. The precipitated crystals are collected by filtration, washed with cold water and dried at 50° C. to give the (−)-(2R,3R)-isomeric salt (0.40 g) mentioned above.

[α]$^{25}_D$:−83.2° (c=1, MeOH); Optical purity 96.3% ee

IR and NMR spectra of the product are identical with those of the product in Reference Example 2.

Subsequently, the optically active (+)-(2S,3S)- and (−)-(2R,3R)-isomeric salts can be obtained by repeated resolution (8 times) in the same manner as described above (the detailed conditions are shown in Table 1). Meanwhile, the result (yield, optical purity and resolution ratio) of each resolution is shown in Table 2.

TABLE 1

| | composition of the solution | | | | | |
| | | | excess | conditions of crystallization | | |
| No. | amount of racemic salt added (*1) (g) (A1) | racemic salt (g) (A2) | amount of (+)- or (−)-isomeric salt (g) (B) | amount of seed crystals (g) (C) | time (hr) | temp. (° C.) |
| --- | --- | --- | --- | --- | --- | --- |
| 1 | 0.31 | 5.02 | 0.16(+) | 0.03 | 3 | 40 |
| 2 | 0.20 | 5.02 | 0.10(−) | 0.03 | 4 | 40 |
| 3 | 0.17 | 5.02 | 0.08(+) | 0.03 | 6 | 40 |
| 4 | 0.21 | 5.02 | 0.10(−) | 0.03 | 6 | 40 |
| 5 | 0.19 | 5.02 | 0.10(+) | 0.03 | 8 | 40 |
| 6 | 0.24 | 5.02 | 0.12(−) | 0.03 | 7 | 40 |
| 7 | 0.26 | 5.02 | 0.13(+) | 0.03 | 9 | 40 |
| 8 | 0.27 | 5.02 | 0.13(−) | 0.03 | 8 | 40 |

(*1): A1 means the amount of racemic salt which was added to the mother liquor obtained after the previous crystallization in order to adjust the contents of the racemic salt (5.02 g) therein.

TABLE 2

| No. | crystals separated yield (g) (D) | optical purity (% ee) (E) | resolution rate (*2) (%) |
|---|---|---|---|
| 1 | 0.29 (+) | 97.6 | 3.7 |
| 2 | 0.22 (−) | 97.3 | 3.7 |
| 3 | 0.22 (+) | 98.2 | 3.8 |
| 4 | 0.23 (−) | 97.6 | 3.8 |
| 5 | 0.25 (+) | 97.8 | 5.0 |
| 6 | 0.28 (−) | 97.2 | 4.9 |
| 7 | 0.29 (+) | 93.7 | 4.8 |
| 8 | 0.31 (−) | 95.2 | 5.8 |

(*2): The resolution rate (%) is calculated by the following formula.

$$\text{Resolution rate}(\%) = \frac{[(D) \times (E)/100] - (B) - (C)}{(A2) \times 0.5} \times 100$$

EXAMPLE 4

Conversion of (+)-(2S, 3S)-cis-5-[2-(dimrethylamino) ethyl]-2,3-dihydro-3-hydroxy-2-(4-methoxyphenyl)-1,5-benzothiazepin-4(5H)-one. 2-aminophenol-4-sulfonate the free base thereof.

(+)-(2S, 3S)-cis-5-[2-(Dimethylamino) ethyl]-2,3-dihydro-3-hydroxy-2-(4-methoxyphenyl)-1,5-benzothiazepin-4(5H)-one. 2-aminophenol-4-sulfonate (0.56 g) (1 mmol;97.8% ee) is dissolved in water (30 ml) under heating and sodium hydrogen carbonate (0.09 g;1.1 mmol) is added thereto. The mixture is extracted with ethyl acetate. The extract is washed with water and concentrated to dryness to give (+)-(2S, 3S)-cis-5-[2-(dimehylamino) ethyl]-2,3-dihydro-3-hydroxy-2-( 4-methoxyphenyl)-1,5-benzothiazepin-4(5H)-one (0.35 g;93.0%).

M.p. 84–86° C.

$[\alpha]^{25}_D$:+166.1° (c=1, MeOH); Optical purity: 98.0% ee

IR (KBr) cm$^{-1}$:2825, 1670, 1610, 1510, 1470, 1440, 1365, 1305, 1255, 1180, 1130, 770. NMR (200 MHz, DMSO-d$_6$) δ :2.14 (s, 6H), 2.22–2.35 (m, 1H), 2.49–2.62 (m, 1H), 3.63–3.76 (m, 1H), 3.76 (s, 3H), 4.20 (t, 1H), 4.26–4.41 (m, 1H), 4.50 (d, 1H), 4.89 (d, 1H), 6.87–7.70 (m, 8H).

Effects of the invention

According to the present invention, the optically active 1,5-benzothiazepine compounds which are important as an intermediate for preparing diltiazem can be readily obtained in a high optical purity without using an expensive optically active resolving agent. Therefore, the method of the present invention is advantageous for preparing the optically active benzothiazepine compounds in an industrial scale.

What is claim is:

1. A process for obtaining an optically active salt of a cis-3-hydroxy-1,5-benzothiazepine compound of formula (I) from a racemic salt of the 1,5-benzothiazepine compound of formula (I):

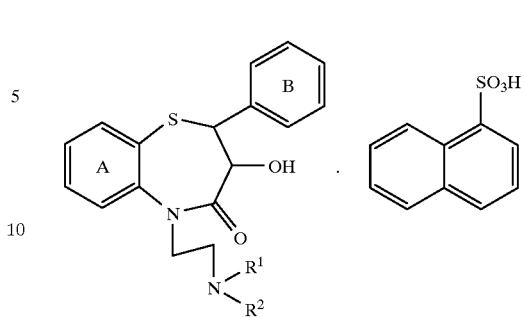

(I)

wherein each of Ring A and Ring B is a substituted or unsubstituted benzene ring, and R$^1$ and R$^2$ are the same or different and each is a lower ailkyl group, the process comprising a step of optically resolving the racemic salt of the 1,5-benzothiazepine compound of formula (I) by means of preferential crystallization, wherein said racemic salt has been formed from a cis-3-hydroxy-1,5-benzothiazepine.

2. A process for obtaining an optically active salt of a cis-3-hydroxy-1,5-benzothiazepine compound of formula (I) from a racemic salt of the 1,5-benzothiazepine compound of formula (I):

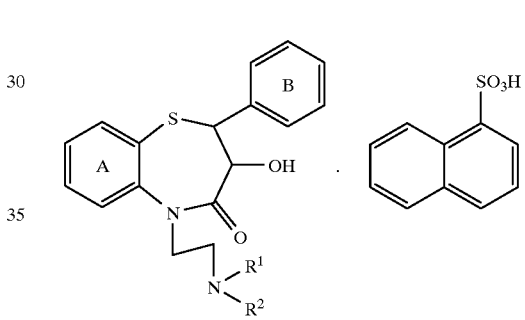

(I)

wherein each of Ring A and Ring B is a substituted or unsubstituted benzene ring, and R$^1$ and R$^2$ are the same or different and each is a lower alkyl group, the process comprising:

dissolving a 1,5-benzothiazepine compound and 1-naphthalenesulfonic acid in an appropriate solvent under heating;

cooling the solution;

subjecting the resulting solution to preferential crystallization by obtaining a supersaturated solution of the racemic salt (I);

inoculating seed crystals of a desired optically active salt of the corresponding (2S,3S)-isomer or the (2R,3R)-isomer into the solution to precipitate preferentially the same crystals as the inoculating salt; and collecting the precipitated crystals by filtration.

3. The process according to claim 1, wherein Ring A is an unsubstituted benzene ring, Ring B is a benzene ring substituted with a methoxy group at 4-position thereof and R$^1$ and R$^2$ are methyl group.

4. The process according to claim 3, wherein the optically active salt of 1,5-benzothiazepine compound of the formula (I) is the optically active (2S, 3S)-isomeric salt.

5. The process according to claim 3, wherein a mother liquor obtained after the crystallization of the optically active salt (I) is further subjected to optical resolution by means of preferential crystallization after addition of the racemic salt (I) to the mother liquor.

6. A process for obtaining an optically active cis-3-hydroxy-1,5-benzothiazepine compound of formula (III):

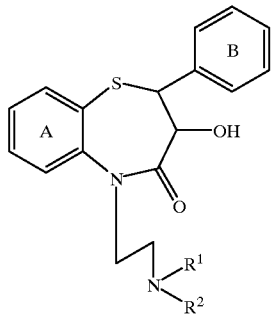

(III)

wherein each of Ring A and Ring B is a substituted or unsubstituted benzene ring, and $R^1$ and $R^2$ are the same or different and each is a lower alkyl group, the process comprising obtaining the optically active salt of the cis-3-hydroxy-1,5-benzothiazepine compound (I) according to the process of claim 1, 3, 4, 5, or 2, and converting the optically active salt (I) into a corresponding free base of formula (III).

7. A process for obtaining an optically active 1,5-benzothiazepine compound of formula (IV):

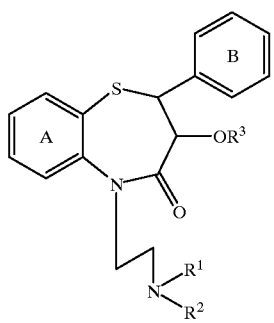

(IV)

wherein each of Ring A and Ring B is a substituted or unsubstituted benzene ring, $R^1$ and $R^2$ are the same or different and each is a lower alkyl group, and $R^3$ is a lower alkanoyl group, or a pharmaceutically acceptable salt thereof, the process comprising obtaining the optically active compound (III) according to the process of claim 6, and converting the optically active compound (III) into the optically active 1,5-benzothiazepine compound (IV) or a pharmaceutically acceptable sat thereof.

8. A salt of a cis-3-hydroxy-1,5-benzothiazepine compound of formula (I):

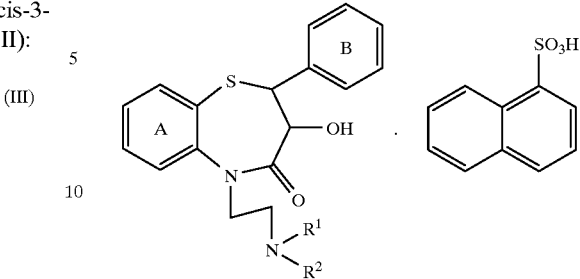

(I)

wherein each of Ring A and Ring B is a substituted or unsubstituted benzene ring, and $R^1$ and $R^2$ are the same or different and each is a lower alkyl group.

9. The optically active salt of a 1,5-benzothiazepine compound according to claim 8, wherein Ring A is an unsubstituted benzene ring, Ring B is a benzene ring substituted by a methoxy group at the 4-position thereof, and $R^1$ and $R^2$ are each a methyl group.

10. The process according to claim 1, wherein the optical resolution step includes producing a supersaturated solution of the racemic salt of the 1,5-benzothiazepine compound (I).

11. The process according to claim 10, wherein the optical resolution step includes inoculating seed crystals of the optically active salt of the 1,5-benzothiazepine compound (I) into the supersaturated solution.

12. The process according to claim 11, further comprising isolating crystals of the optically active salt of the 1,5-benzothiazepine compound (I) produced during preferential crystallization to provide a crystal product and a mother liquor.

13. The process according to claim 12, further comprising adding additional racemic salt of the 1,5-benzothiazepine compound (I) to the mother liquor to produce a second supersaturated solution; and subjecting the second supersaturated solution to optical resolution by means of a second preferential crystallization.

14. The process according to claim 13 wherein the second preferential crystallization includes inoculating seed crystals of the optically active salt of the 1,5-benzothiazepine compound (I) into the second supersaturated solution.

15. The process according to claim 10, wherein the supersaturated solution is rich in a first isomer corresponding to the optically active salt of the 1,5-benzothiazepine compound (I) as compared to other isomers in the racemic salt of the 1,5-benzothiazepine compound (I).

16. The process according to claim 2, wherein Ring A is an unsubstituted benzene ring, Ring B is a benzene ring substituted with a methoxy group at the 4-position thereof and $R^1$ and $R^2$ are each a methyl group.

17. The process according to claim 16, wherein the optically active salt of the 1,5-benzothiazepine compound of formula (I) is the optically active (2S,3S)-isomeric salt.

18. (+)-(2S,3S)-cis-5-[2-(dimethylamino) ethyl]-2,3-dihydro-3-hydroxy-2-(4-methoxyphenyl)-1,5-benzothiazepin-4(5H)-one•1-naphthalenesulfonate.

* * * * *

UNITED STATES PATENT AND TRADEMARK OFFICE
CERTIFICATE OF CORRECTION

PATENT NO. : 5,929,068
DATED : July 27, 1999
INVENTOR(S) : Ryuzo YOSHIOKA et al

It is certified that error appears in the above-identified patent and that said Letters Patent is hereby corrected as shown below:

Claim 1, col. 10, line 17, "ailkyl" should read --alkyl--.

Claim 3, col. 10, line 60, before "4-position", insert --the--.

Claim 3, col. 10, line 61, before "methyl", insert --each a--.

Claim 4, col. 10, line 63, before "1,5-benzothiazepine", insert --the--; and before "formula", delete "the".

Claim 7, col. 11, line 56, "sat" should read --salt--.

Claim 14, col. 12, line 40, after "claim 13", insert --,--.

Signed and Sealed this

Second Day of May, 2000

Attest:

Attesting Officer

Q. TODD DICKINSON

Director of Patents and Trademarks